(12) United States Patent
Mire et al.

(10) Patent No.: US 8,617,062 B2
(45) Date of Patent: Dec. 31, 2013

(54) OVER DILATION

(75) Inventors: David A. Mire, Cordova, TN (US); Kelli N. Sebastian, Arlington, TN (US); Paul F. Wheeler, Hernando, MS (US); John A. Elliott, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 408 days.

(21) Appl. No.: 12/832,146

(22) Filed: Jul. 8, 2010

(65) Prior Publication Data

US 2012/0010471 A1  Jan. 12, 2012

(51) Int. Cl.
*A61B 17/02* (2006.01)

(52) U.S. Cl.
USPC ......... 600/210; 606/108; 606/191; 604/164.1

(58) Field of Classification Search
USPC ......... 600/203–208, 215, 219, 233, 236–237; 606/191, 198, 108; 604/164.1, 164.03, 604/164.11, 164.09; 138/161, 166; 248/161, 157, 125.8
See application file for complete search history.

(56) References Cited

U.S. PATENT DOCUMENTS

| | | | |
|---|---|---|---|
| 4,998,326 A * | 3/1991 | Oetiker | 24/20 R |
| 5,171,279 A | 12/1992 | Mathews | |
| 5,792,044 A | 8/1998 | Foley et al. | |
| 5,954,635 A | 9/1999 | Foley et al. | |
| 6,159,179 A | 12/2000 | Simonson | |
| 6,743,207 B2 | 6/2004 | Elbert et al. | |
| 7,008,431 B2 | 3/2006 | Simonson | |
| 7,074,226 B2 | 7/2006 | Roehm, III et al. | |
| 7,427,264 B2 | 9/2008 | Nowitzke et al. | |
| 7,618,431 B2 | 11/2009 | Roehm, III et al. | |
| 7,691,057 B2 | 4/2010 | Miles et al. | |
| 2003/0083688 A1 | 5/2003 | Simonson | |
| 2004/0059339 A1 | 3/2004 | Roehm, III et al. | |
| 2004/0064147 A1 * | 4/2004 | Struble | 606/129 |
| 2005/0004593 A1 | 1/2005 | Simonson | |
| 2005/0216002 A1 | 9/2005 | Simonson | |
| 2006/0030861 A1 | 2/2006 | Simonson et al. | |
| 2006/0247651 A1 | 11/2006 | Roehm, III et al. | |
| 2007/0100366 A1 | 5/2007 | Dziedzic et al. | |
| 2007/0142778 A1 | 6/2007 | Elbert et al. | |
| 2010/0113884 A1 | 5/2010 | Miles et al. | |

* cited by examiner

*Primary Examiner* — Robyn Doan
*Assistant Examiner* — Jessica Weiss

(57) ABSTRACT

A device, system and method for dilating a patient during a minimally invasive surgical procedure is disclosed. A surgical dilation system includes a dilator having an outer tubular member and an inner tubular member sized to be movably received within an inside diameter of the outer tubular member. The outer tubular member includes a vertical slot running through a side of the outer tubular member. The inner tubular member has an upper portion and a lower portion. The retractor has a proximal end including at least one mounting member protruding outwardly from a side surface of the retractor and a distal end including at least one fanned blade protruding outwardly from the side surface. When the inner tubular member is oriented in a first position the vertical slot is in a closed state, when the inner tubular member is oriented in a second position the mounting member is permitted to travel downwardly a predetermined distance in the vertical slot, and when the inner tubular member is positioned in a third state the mounting member is permitted to freely travel through the vertical slot.

6 Claims, 11 Drawing Sheets

OVER DILATION

BACKGROUND

The present invention relates generally to percutaneous surgeries and more particularly, to devices, methods and systems for performing percutaneous, minimally invasive spinal surgeries.

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require a recovery room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

Minimally invasive alternatives such as arthroscopic techniques reduce pain, post-operative recovery time and the destruction of healthy tissue. Orthopedic surgical patients have particularly benefited from minimally invasive surgical techniques. The site of pathology is accessed through portals rather than through a significant incision thus preserving the integrity of the intervening tissues. In some instances, these minimally invasive techniques require only local anesthesia. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with the muscle dissection.

In order to reduce the post-operative recovery time and pain associated with spinal and other procedures, micro-surgical techniques have been developed. The objective of any minimally invasive procedure is to accomplish the same clinical objectives as the traditional, open surgery while minimizing soft tissue retraction. Existing sequential dilation processes consist of inserting multiple increasing diameter dilators until the correct diameter is achieved. A tubular retractor is then placed over the dilators and the dilators are then removed. The retractor is left in place with the surrounding muscle and tissue having been dilated out of the working space.

For some applications, it is beneficial to have an alternate blade shape on the distal tip of the retractor to assist in holding back muscle and tissue during the procedure. As such, a need exists for a device that will allow alternate blade shapes to be used during the dilation process.

SUMMARY

According to one aspect a surgical dilator is disclosed that is configured to dilate an incision and tissue in a patient. The surgical dilator includes an outer tubular member having a vertical slot running along a vertical axis from a distal end of the outer tubular member to a proximal end of the tubular member. An inner tubular member is sized and configured to be received within an interior of the outer tubular member. The inner tubular member includes an upper portion having a generally semi-circular cross-sectional shape along a horizontal axis transitioning to a lower portion having a tubular shape with a slot therein. The inner tubular member is operable to be movably positioned in a first position in which the upper portion and the lower portion close the vertical slot in the outer tubular member, a second position in which the lower portion closes the vertical slot, and a third position in which the vertical slot is exposed.

In one form, the outer tubular member includes a head portion having a vertical groove transitioning downwardly from an upper surface of the head portion to a predetermined depth in the head portion. The head portion includes an internal circumferential groove connected with the vertical groove. The inner tubular member includes a protrusion extending outwardly from the upper portion of the inner tubular member that is sized to fit within the vertical and circumferential grooves. The outer tubular member includes a first head portion upon which a lower surface of a second head portion of the inner tubular member rests when the inner tubular member is positioned within the outer tubular member. In yet another form, the inner tubular member includes a protrusion that is positioned within a guide track that is formed in the first head portion.

According to another aspect, a surgical dilator is disclosed that is configured to dilate an incision and tissue in a patient. As with the previous aspect, the surgical dilator includes an outer tubular member including a slot running along a vertical axis of the outer tubular member and a head portion having a larger outside diameter than an insertion portion of the outer tubular member. The head portion of the outer tubular member includes a guide track. An inner tubular member is sized to be received within the outer tubular member. The inner tubular member has a protrusion that is sized to be received within the guide track such that movement of the inner tubular member is restricted by the guide track. In another form, an inner surface of the outer tubular member is configured with a protrusion that is configured to be received within a guide track located on an outer surface of the inner tubular member.

The inner tubular member has an upper portion having a generally semi-circular cross-sectional shape along a horizontal axis and a lower portion having a slot. The inner tubular member is configured to be rotated within the guide track such that in a first position the inner tubular member completely closes off access to the vertical slot, a second position in which the upper portion of the inner tubular member exposes the vertical slot, and a third position in which the vertical slot is entirely exposed.

In one form, the inner tubular member includes a second head portion at a proximal end of the inner tubular member that is configured to rest on an upper surface of the head portion of the outer tubular member when the protrusion is positioned within the guide track. A lower end of the outer and inner tubular members can include an inwardly tapered tip. The guide track is defined by a vertically oriented groove connected with a circumferential groove formed in an interior wall of the head portion.

According to yet another aspect, a surgical dilation system is disclosed that is configured to dilate an incision and tissue in a patient and then retract the incision and tissue. The surgical dilation system includes a dilator having an outer tubular member and an inner tubular member sized to be movably received within an inside diameter of the outer tubular member. The outer tubular member includes a vertical slot running through a side of the outer tubular member. The inner tubular member has an upper portion and a lower portion. The retractor has a proximal end including at least one mounting member protruding outwardly from a side surface of the retractor and a distal end including at least one fanned blade protruding outwardly from the side surface. When the inner tubular member is oriented in a first position the vertical slot is in a closed state, when the inner tubular member is oriented in a second position the mounting member is permitted to travel downwardly a predetermined distance in the vertical slot, and when the inner tubular member is positioned in a third state the mounting member is permitted to freely travel through the vertical slot.

In one form, the upper portion of the inner tubular member has a generally semi-circular cross-sectional shape along a horizontal axis. The lower portion of the inner tubular member has a second vertical slot running therethrough having a size at least as wide the vertical slot in the outer tubular member. The outer tubular member has a head portion having a guide track formed therein. The upper portion of the inner tubular member includes a protrusion sized to be received in the guide track. The inner tubular member includes a second head portion having a lower surface that rests on an upper surface of the head portion of the outer tubular member. In one form, the lower portion of the inner tubular member includes a first tapered end and a lower portion of the outer tubular member includes a second tapered end that facilitates insertion of the dilator into the patient.

Related features, aspects, embodiments, objects and advantages of the present invention will be apparent from the following description.

DESCRIPTION OF THE ILLUSTRATED EMBODIMENTS

Figure 1:
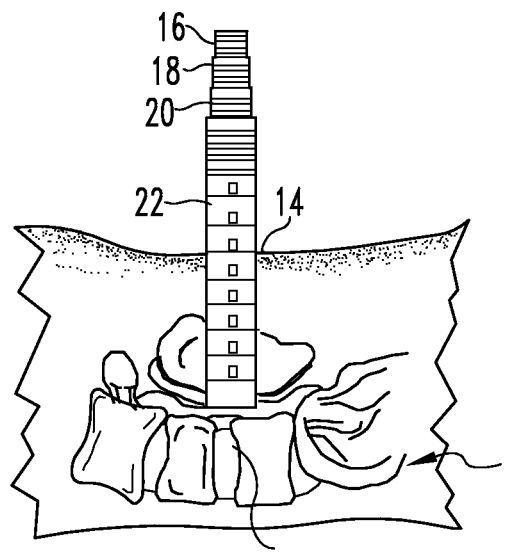
FIG. 1 illustrates a dilation device that comprises a plurality of interconnected dilators each having a larger outside diameter than the other inserted into an incision of a patient.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 2:
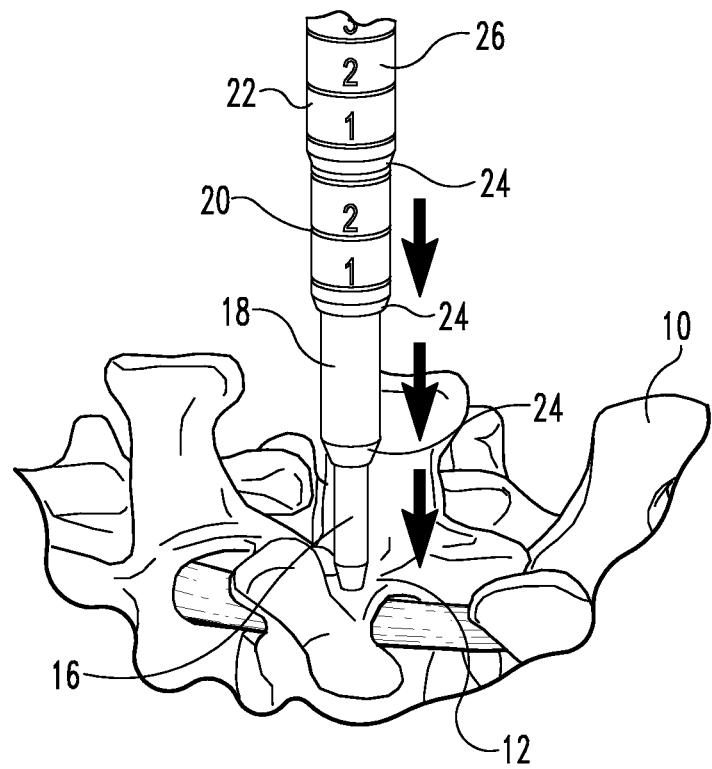
FIG. 2 illustrates another view of the dilation device illustrated in FIG. 1.

Referring collectively to FIGS. 1 and 2, a system, device and method for use in connection with a lumbar discectomy in which an affected nerve root is to be decompressed will be generally discussed. Although a lumbar discectomy is described herein, it should be readily appreciated that the principles of the present invention can be applied to many other types of percutaneous, minimally invasive surgical procedures as well. As such, the fact that a lumbar discectomy is described in connection herewith should not be construed in any way as a limitation of the present invention unless expressly set forth in the claims.

A discectomy procedure typically begins with a surgeon precisely locating the herniated disc with a very small needle that is inserted through the muscles of the back down to an area of the spine 10 where spinal disc fragments 12 are located. The correct position of the needle is typically confirmed using a fluoroscope, although the use of any imaging technology is contemplated herein. Once this is accomplished, the needle is removed and a small incision 14 is made at the puncture site. Typically, the incision 14 length will match the outside diameter of the largest tubular dilator (e.g. ~21 millimeters), which will be discussed in detail below. A guide wire (not shown) may then be inserted into the incision 14 and placed in the proper position in relation to the disc fragments 12 that are to be removed. Again, a fluoroscope may be used to confirm that the guide wire is placed in the proper position.

Once the guide wire is placed in the proper position, a first cannulated soft tissue dilator 16 is inserted over the guide wire and through the incision 14 to a desired depth. At this point, the guide wire can be removed from within the first cannulated soft tissue dilator 16. The first cannulated soft tissue dilator 16 may then be used to palpate the incision in both the sagittal and coronal planes. In one form, the first dilator 16 may have an outside diameter of 12 millimeters, for example. Next, second, third, and fourth cannulated soft tissue dilators 18, 20, 22 are sequentially placed over one another and inserted through the incision 14 to the desired depth. In the illustrated form, a distal end 24 of each cannulated soft tissue dilator has a tapered portion to help facilitate insertion through the incision 14 and related muscle and tissue. Further, in other forms, one or more of the cannulated soft tissue dilators disclosed herein may include depth indicators or markings 26 on an outside surface to help inform the surgeon as to what depth the cannulated soft tissue dilators have been inserted into the patient.

In one illustrative form, the second cannulated soft tissue dilator 18 has an outside diameter of 14 millimeters, the third cannulated soft tissue dilator 20 has an outside diameter of 18 millimeters, and the fourth cannulated soft tissue dilator 22 has an outside diameter of 20 millimeters. Although four cannulated soft tissue dilators 16, 18, 20, 22 are utilized in the illustrated form, it should be appreciated that any number of cannulated soft tissue dilators could be used in other forms of the present invention. Further, the outside diameters of the cannulated soft tissue dilators could also vary in size in other forms of the present invention and the illustrative diameters set forth above should not be construed as a limitation of the present invention. The cannula or hollow interior portions of each cannulated soft tissue dilator is sized to fit or slide over the outside diameter of other respective dilators. In still other forms of the present invention, dilator 50, as discussed further below, is inserted into the patient without the use of sequential dilation.

Figure 3:
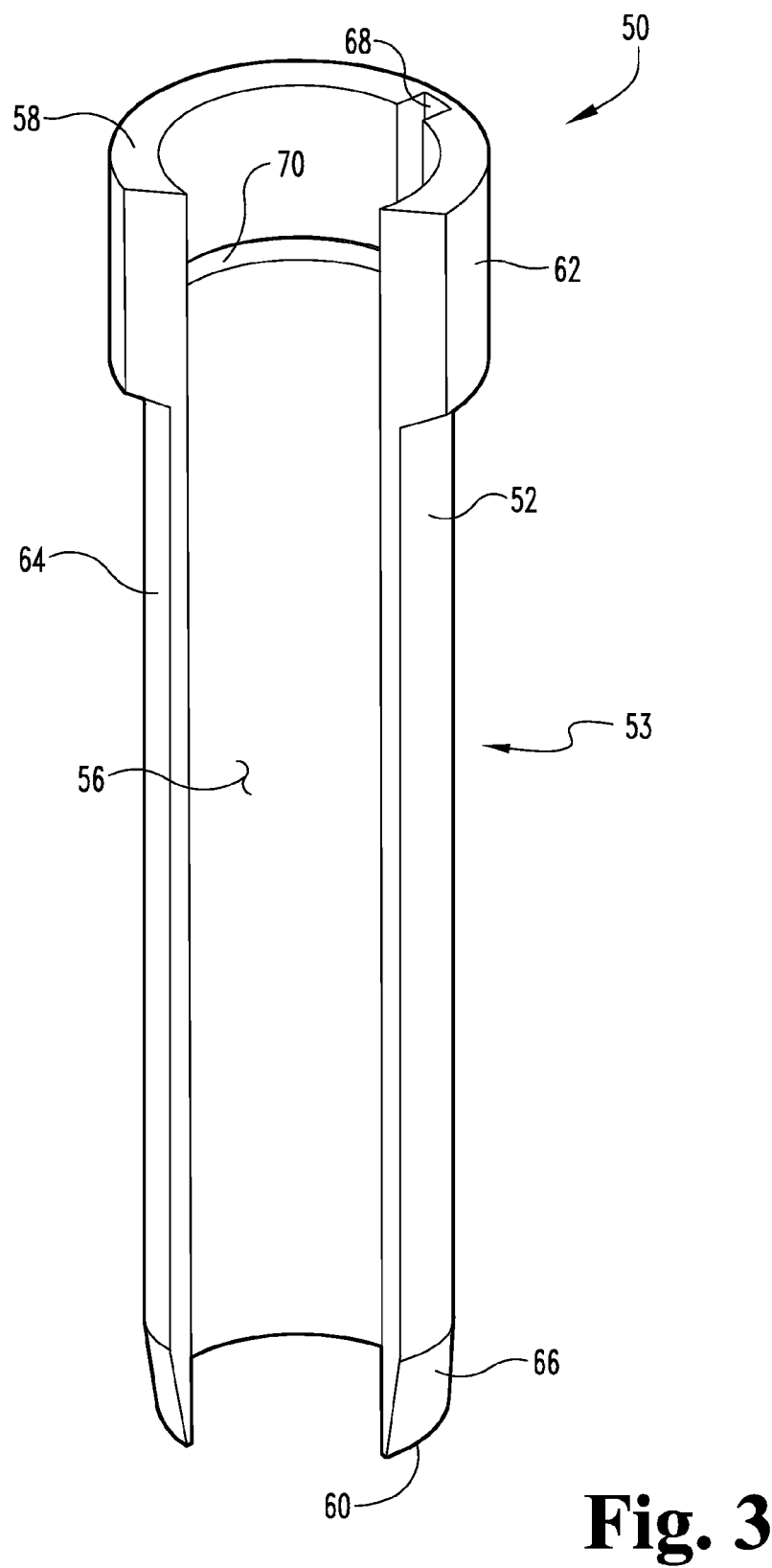
FIG. 3 is a perspective view of an outer tubular member of a representative dilator.
Figure 4:
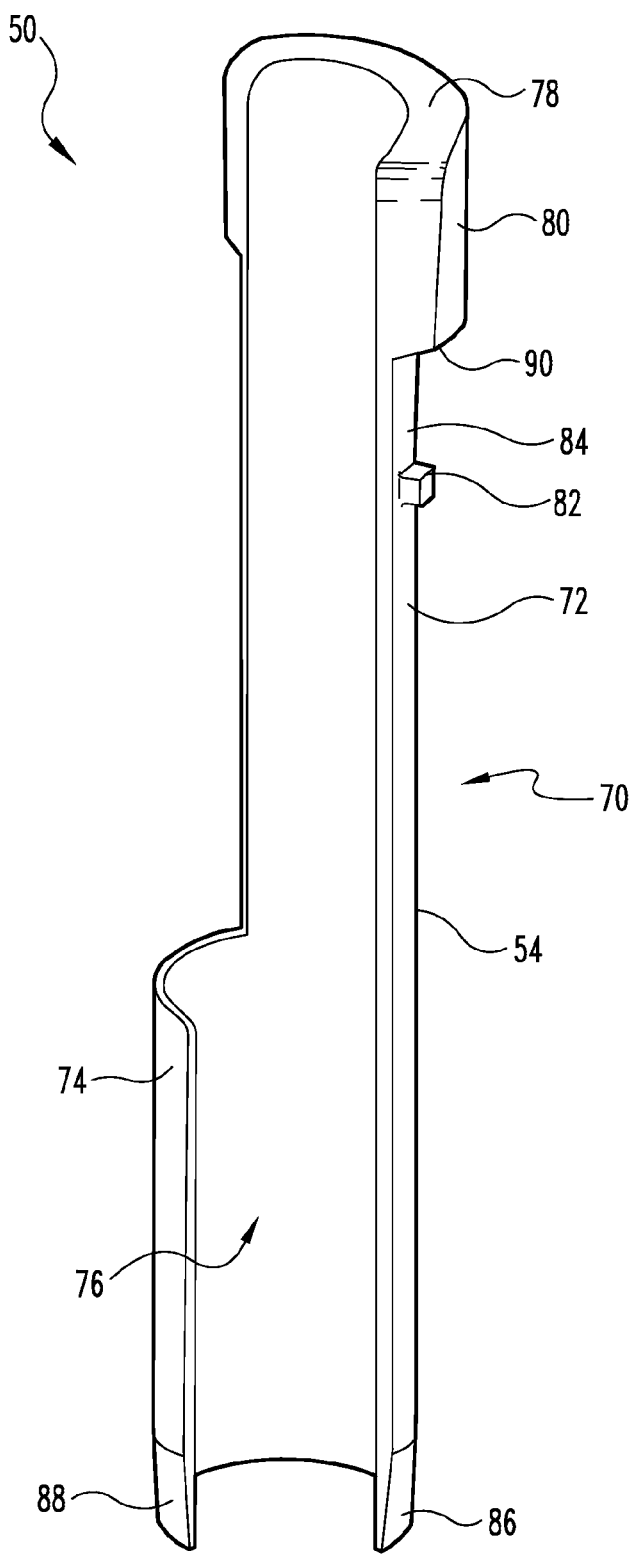
FIG. 4 is a perspective view of an inner tubular member of a representative dilator.

Referring collectively to FIGS. 3 and 4, one representative aspect discloses a dilator 50 that includes an outer tubular member 52 and an inner tubular member 54. As described in greater detail below, the inner tubular member 54 is sized and configured to be slidably received within the inside diameter of the outer tubular member 52. The outer tubular member 52 includes a body 53 that has a circular cross-section shape that includes a vertical slot 56 running from a proximal end 58 to a distal end 60 of the body 53. The proximal end 58 of the body 53 defines a head portion 62 that has a larger outside diameter than an insertion portion 64 of the body 53. As illustrated, the head portion 62 transitions to the insertion portion 64 with the insertion portion 64 having a longer length than the head portion 62. The distal end 60 of the body 53 includes an inwardly tapered portion 66 to help facilitate insertion through the incision 14.

The head portion 62 of the outer tubular member 52 also includes a generally vertical inwardly facing groove or passage 68 and a circumferential groove or passage 70. The vertical groove 68 transitions into and/or is connected with the circumferential groove 70 thereby providing interconnected grooves. In one form, the groove 68 runs substantially vertical along a vertical axis, but in other forms the groove 68 could be diagonal or angled down toward the circumferential groove 70. In one form, the circumferential groove 70 runs almost, but not entirely, around the circumference of the inside diameter of the outer tubular member 52. The circumferential groove 70 stops just before reaching each side of the slot 56. In another form, the circumferential groove 70 is configured to stop the inner tubular member 54 in open and closed states. The vertical and circumferential grooves 68, 70 form a guide track in the head portion 62 of the outer tubular member 52.

As set forth above, the inner tubular member 54 is sized and configured to be slidably received within the inside diameter of the outer tubular member 52. The inner tubular member 54 has a generally semi-circular cross-sectional shaped upper portion 72 along a horizontal axis and a tubular shaped lower portion 74 that includes a slot 76. The tubular slot 76 is sized to have the same width as the slot 56 in the outer tubular member 52. A proximal end 78 of the semi-circular cross-sectional shaped upper portion 72 includes a generally semi-circular cross-sectional shaped tubular head portion 80. The tubular head portion 80 has a larger outside diameter than the upper portion 72 and protrudes outwardly therefrom a predetermined distance. The upper portion 72 includes a protrusion 82 extending outwardly from an outside surface 84 of the upper portion 72. As set forth below, the protrusion 82 is sized and configured to be received in the vertical and circumferential internal grooves 68, 70 of the outer tubular member 52. A distal end 86 of the tubular shaped lower portion 74 includes a tapered portion 88 to facilitate insertion of the dilator 50 through the incision 14. It should also be appreciated that the vertical and circumferential grooves 68, 70 could be located on the inner tubular member 54 facing the outer tubular member 52 and that the protrusion 82 could be located on the outer tubular member 52 facing the inner tubular member 54. In other words, the orientation of the vertical and circumferential grooves 68, 70 and the protrusion 82 are reversed in this form. In one form, the outer diameter of head portion 80 encompasses the outer diameter of head portion 62 so that the head portion 80 of the inner tubular member 54 can rotate about the upper surface of the head portion 62 of the outer tubular member 52.

Figure 5:
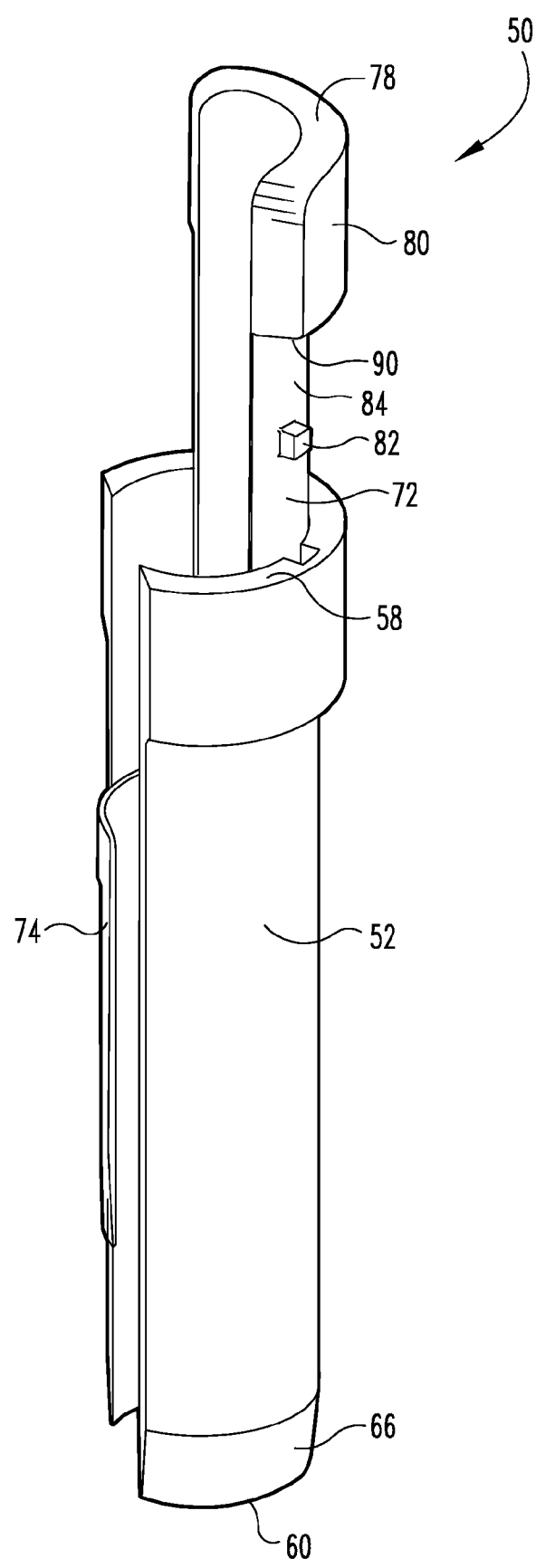
FIG. 5 illustrates a perspective view of the inner tubular member positioned within the outer tubular member.
Figure 6:
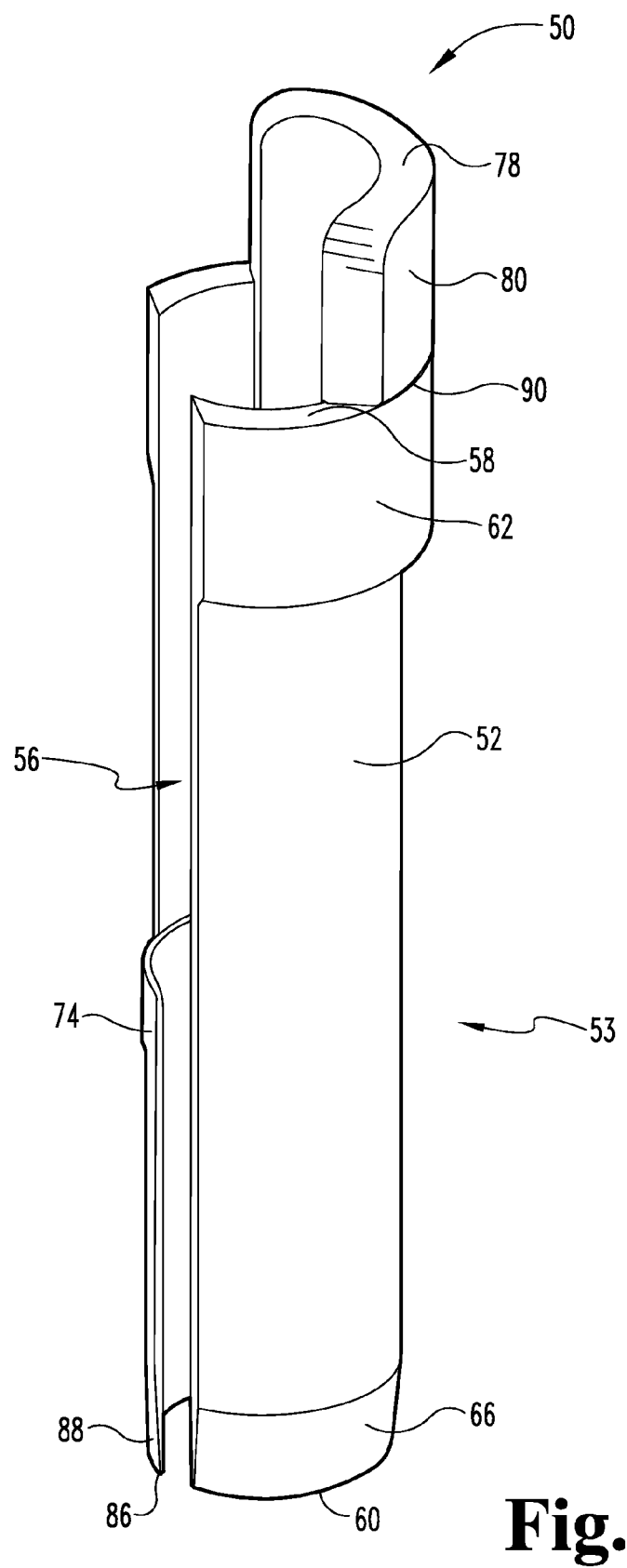
FIG. 6 illustrates another perspective view of the inner tubular member positioned within the outer tubular member.

Referring to FIG. 5, to assemble the dilator 50 the inner tubular member 54 is dropped or positioned inside the outer tubular member 52 such that the protrusion 82 of the inner tubular member 54 fits in or is received within the vertical groove 58 of the outer tubular member 52. The protrusion 82 is positioned or located on the upper portion 72 of the inner tubular member 54 a predetermined distance below a lower or distally facing surface 90 of the head portion 80. As illustrated in FIG. 6, the lower surface 90 of the head portion 80 of the inner tubular member 54 is configured to movably rest on an upper or proximally facing surface 92 of the head portion 62 of the outer tubular member 52 when the inner tubular member 54 is positioned within the outer tubular member 52.

Once fully positioned in the vertical groove 68 of the outer tubular member 52, the inner tubular member 54 can freely rotate horizontally within the circumferential groove 70 of the outer tubular member 52. The protrusion 82 comes into alignment with the circumferential groove 70 thereby allowing rotation of the inner tubular member 54 about the outer tubular member 52. In one form, the circumferential groove 70 does not reach either side of the vertical slot 56 in the outer tubular member 52. The protrusion 82 of the inner tubular member 54 prevents the inner tubular member 54 from travelling around the entire circumference of the outer tubular member 52. Thus, the protrusion 82 freely travels in the guide track formed by the grooves 68, 70. When the inner tubular member 54 is first inserted into the outer tubular member 52, in one form, the tubular shaped lower portion 74 of the inner tubular member 54 partially covers the vertical slot 56 of the outer tubular member 52.

Figure 7:
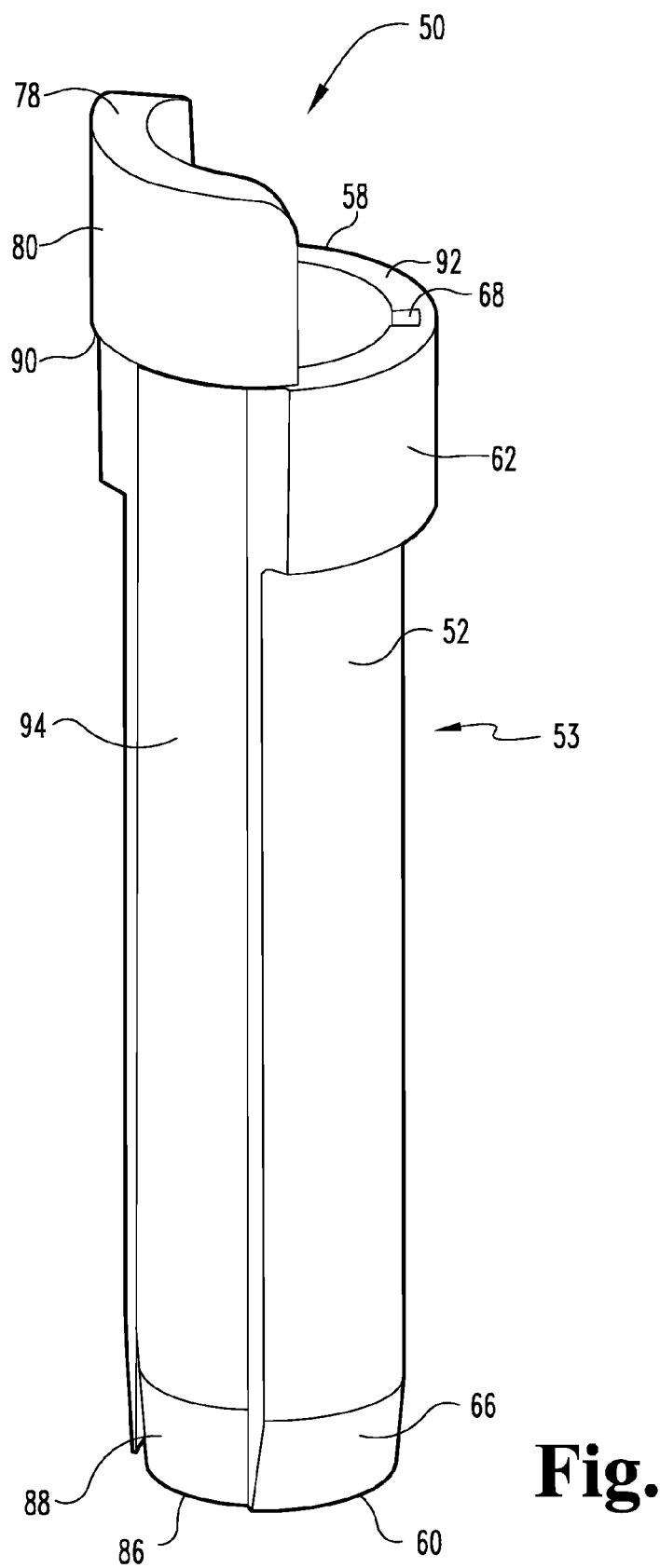
FIG. 7 illustrates another perspective view of the inner tubular member positioned within the outer tubular member.

Referring to FIG. 7, at this point the inner tubular member 54 is circumferentially rotated about the outer tubular member 52 such that the inner tubular member 54 is positioned in a fully closed state in relation to the slot 56 of the outer tubular member 52. In particular, an outer side surface 94 of the inner tubular member 54, formed by the upper portion 72 and a portion of the lower portion 74 of the inner tubular member 54, fully close off the vertical slot 56 in the outer tubular member 54. The dilator 50 is now ready to be inserted into the patient, such as over the fourth dilator 24 referred to in FIGS. 1 and 2 in procedures in which sequential dilation is employed. In such procedures, the dilator 50 is inserted over the outside diameter of the last inserted one of dilators 16, 18, 20, 22. Now, the last inserted one of the initial dilators 16, 18, 20, 22, and any of the other previously inserted dilators not already removed, can be removed from the incision 14 leaving dilator 50 in position in the incision 14.

Figure 8:
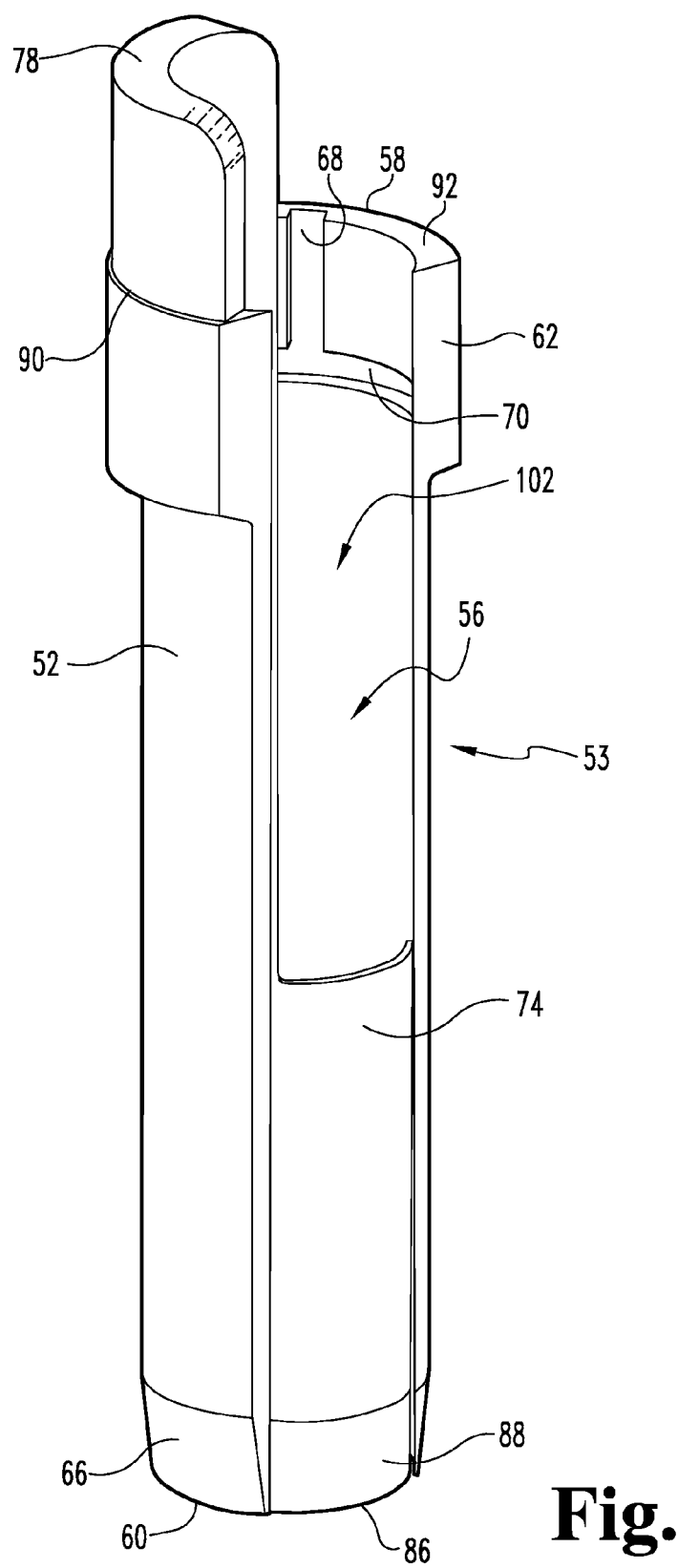
FIG. 8 illustrates another perspective view of the inner tubular member positioned within the outer tubular member.

Referring to FIG. 8, the inner tubular member 54 of dilator 50 is now rotated to a half open position. In particular, inner tubular member 54 is rotated such that the upper portion 72 of the inner tubular member 54 no longer blocks an upper portion of vertical slot 56 of the outer tubular member 52. However, a portion of the lower portion 74 of the inner tubular member 54 still closes off or blocks a lower portion of the vertical slot 56.

Figure 9:
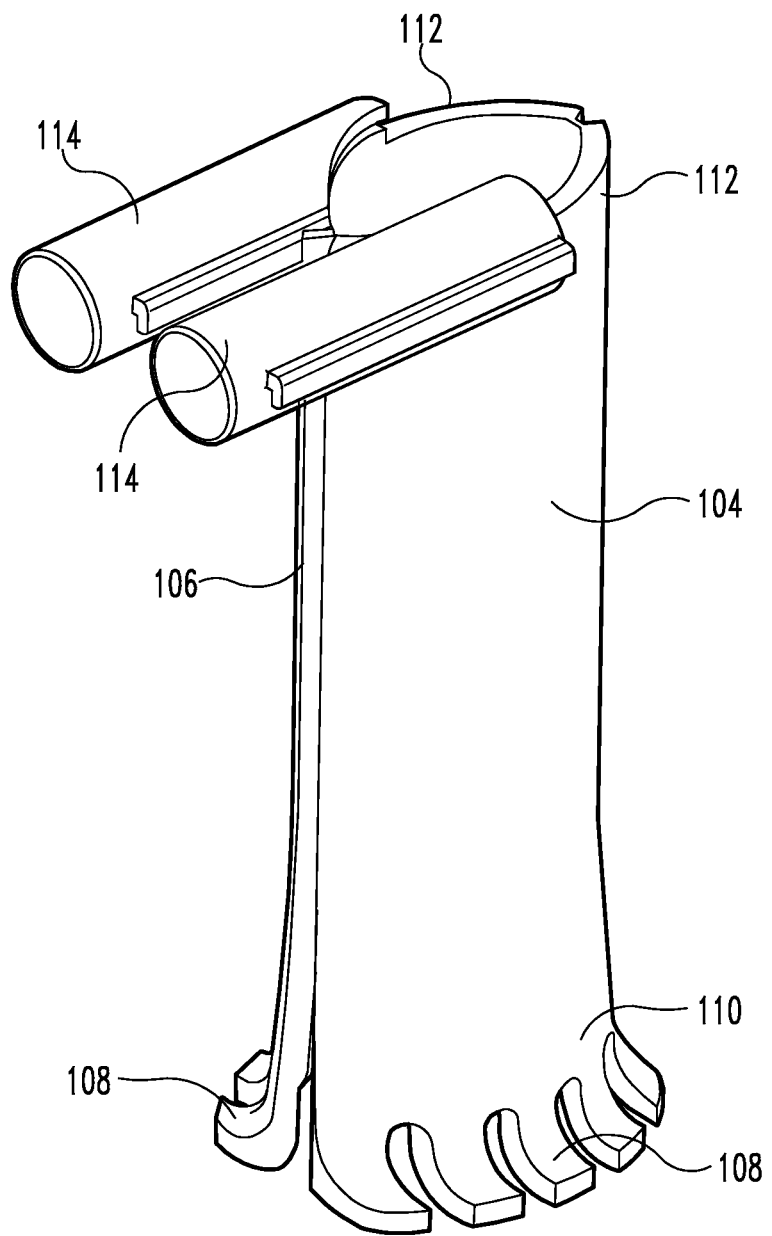
FIG. 9 illustrates a representative retractor having fanned blades.

Referring to FIG. 9, a retractor 100 is illustrated that is sized and configured to fit within an internal passage 102 (see FIG. 8) formed or defined by the outer and inner tubular members 52, 54. In one form, the retractor 100 has a non-circular cross-sectional shape along a horizontal axis but it should be appreciated that retractors having a circular, generally circular, or generally rectangular cross-sectional shape along the horizontal axis can be utilized in other aspects of the present invention. In particular, any cross-sectional shaped retractor 100 can be utilized as long as it is sized to movably fit within the internal passage 102 defined by the outer and inner tubular members 52, 54. The retractor 100 includes a first half 104 and an opposing second half 106 that each have a generally arcuate shape. The first and second halves 102, 104 each include one or more outwardly protruding fanned blades 108 extending from a distally end 110 of the retractor 100. A proximal end 112 of the first and second halves 102, 104 include a cylindrical post 114 extending outwardly from the proximal end 112 of the first and second halves 102, 104. As set forth in greater detail below, the retractor 100 is configured to retract the incision 14 such that a surgical window is formed that provides access to the surgical area of interest.

Figure 10:
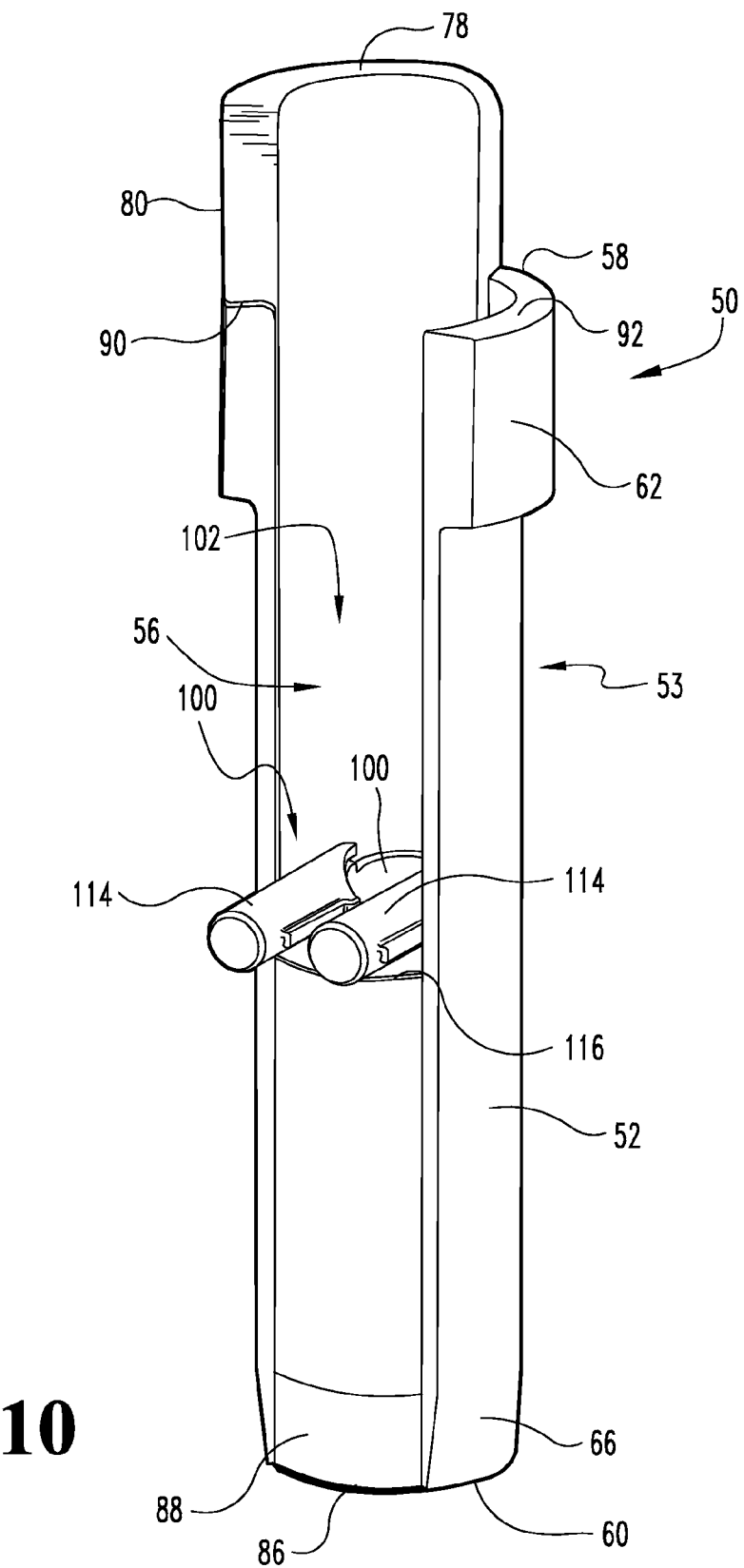
FIG. 10 illustrates a surgical dilation system.
Figure 11:
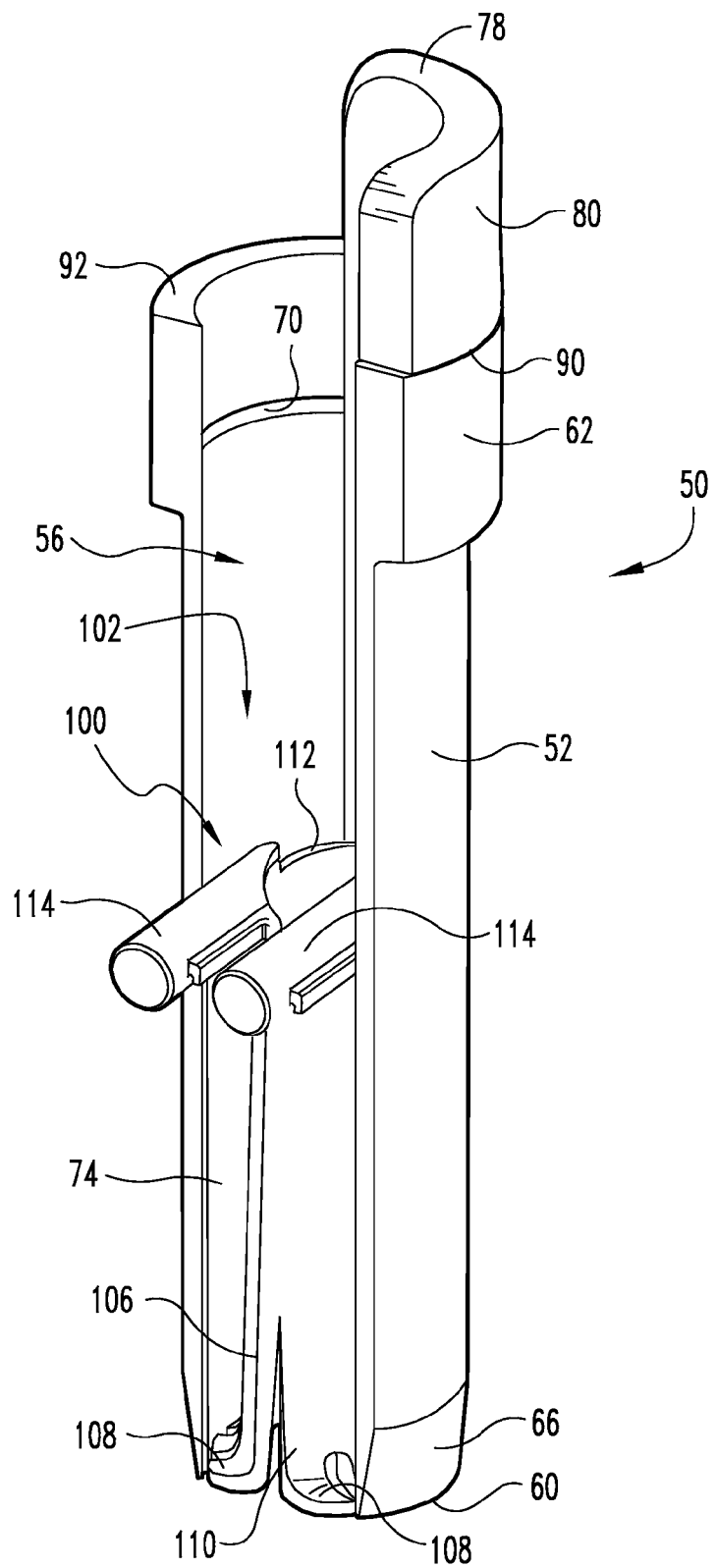
FIG. 11 illustrates another view of the surgical dilation system illustrated in FIG. 10.
Figure 12:
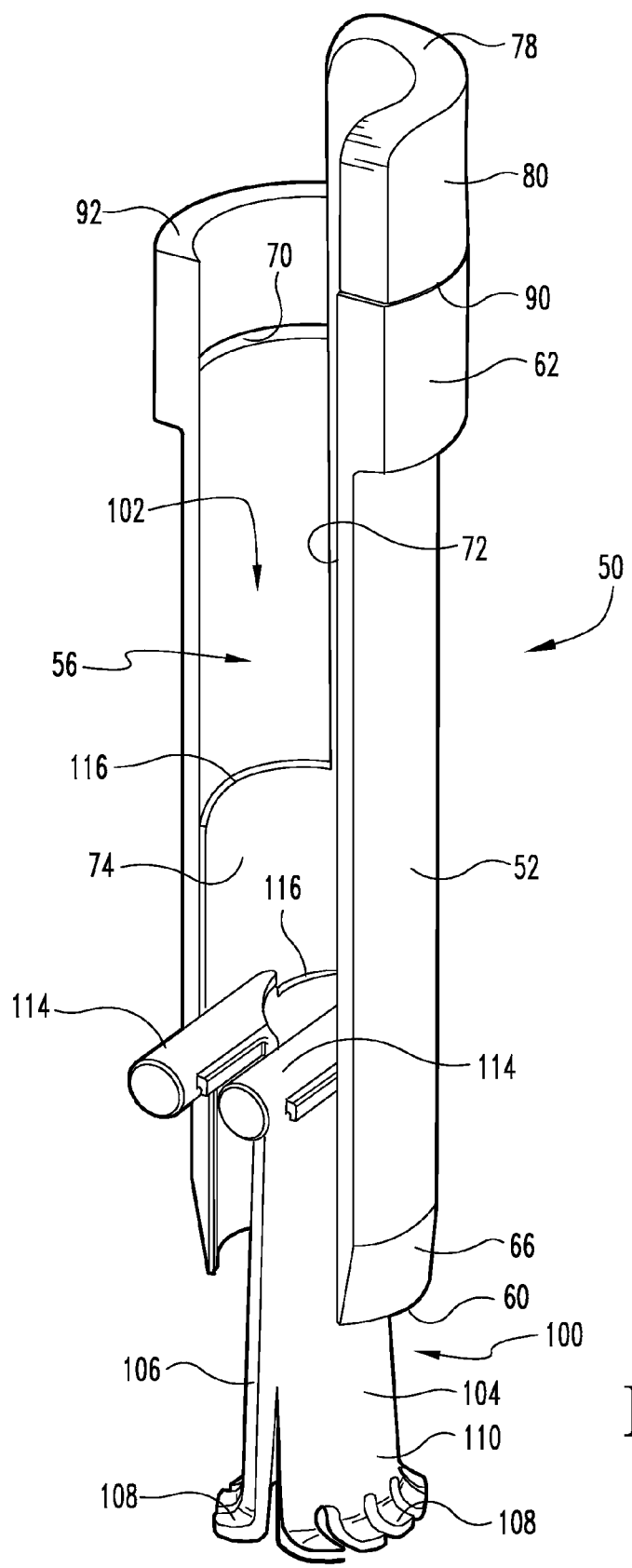
FIG. 12 illustrates another view of the surgical dilation system illustrated in FIG. 10.

Referring to FIG. 10, the retractor 100 is inserted into the internal passage 102 defined by the outer and inner tubular members 52, 54. As illustrated, the retractor 100 is sized and configured to fit within the internal passage 102. In particular, the retractor 100 is inserted such that the posts 114, and thus retractor 100, travel up and down the vertical slot 56 in the outer tubular member 52. After the retractor 100 travels a predetermined distance down the vertical slot 56, the posts 114 of the retractor 100 come into engagement with an upper or proximally facing surface 116 of the lower portion 74 of the inner tubular member 74. As illustrated in FIGS. 11 and 12, at this point the inner tubular member 54 is rotated to a completely open position thereby completely exposing the vertical slot 56 in the outer tubular member 52. The dilator 50 can then be pulled from the incision 14 leaving the retractor 100 in a proper orientation in the incision 14. As set forth above, the retractor 100 can have various different cross-sectional shapes along the horizontal axis of the retractor 100 and the dilator 50 of the present invention can accommodate the extensions, posts or other such features (such as post elements 114) of the retractor 100 regardless of the cross-sectional shape of the retractor 100.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A surgical dilator, comprising: an outer tubular member having a vertical slot running along a vertical axis from a distal end of said outer tubular member to a proximal end of said outer tubular member, wherein said outer tubular member includes a head portion having a vertical groove transitioning downwardly from an upper surface of said head portion to a predetermined depth in said head portion; and an inner tubular member sized and configured to be received within an interior of said outer tubular member, wherein said inner tubular member includes an upper portion having a generally semi-circular cross-sectional shape along a horizontal axis transitioning to a lower portion having a tubular shape with a slot therein, wherein said inner tubular member is operable to be movably positioned in a first position in which said upper portion and said lower portion close said vertical slot in said outer tubular member, a second position in which said lower portion closes said vertical slot, and a third position in which said vertical slot is exposed, and wherein said head portion includes an internal circumferential groove connected with said vertical groove.

2. The surgical dilator of claim 1, wherein said inner tubular member includes a protrusion extending outwardly from said upper portion of said inner tubular member that is sized to fit within said vertical and circumferential grooves.

3. A surgical dilator, comprising:
an outer tubular member including a slot running along a vertical axis of the outer tubular member and a head portion having a larger outside diameter than an insertion portion of the outer tubular member, said head portion having a guide track; and
an inner tubular member sized to be received within said outer tubular member, said inner tubular member having a protrusion sized to be received within said guide track such that movement of said inner tubular member is restricted by said guide track, wherein said inner tubular member has an upper portion having a generally semi-circular cross-sectional shape along a horizontal axis and a lower portion having a slot, and wherein said inner tubular member is configured to be rotated within said guide track such that in a first position said inner tubular member completely closes off access to said vertical slot, a second position in which said upper portion of said inner tubular member exposes said vertical slot, and a third position in which said vertical slot is entirely exposed.

4. A surgical dilator, comprising:
an outer tubular member including a slot running along a vertical axis of the outer tubular member and a head portion having a larger outside diameter than an insertion portion of the outer tubular member, said head portion having a guide track; and
an inner tubular member sized to be received within said outer tubular member, said inner tubular member having a protrusion sized to be received within said guide track such that movement of said inner tubular member is restricted by said guide track, and wherein a lower end of said outer and inner tubular members include an inwardly tapered tip.

5. The surgical dilator of claim 4, wherein said inner tubular member includes a second head portion at a proximal end of said inner tubular member that is configured to rest on an upper surface of said head portion of said outer tubular member when said protrusion is positioned within said guide track.

6. The surgical dilator of claim 4, wherein said guide track is defined by a vertically oriented groove connected with a circumferential groove formed in an interior wall of said head portion.

* * * * *